United States Patent
Nguyen et al.

(10) Patent No.: US 12,102,099 B1
(45) Date of Patent: Oct. 1, 2024

(54) COMPOSITION OF COMPLEX ENZYME-PROBIOTIC AND ITS APPLICATIONS INTO A METHOD FOR PRODUCING A PREPARATION CONTAINING CHLOROGENIC ACID, PROTOCATECHUIC ACID, AND CAFFEIC ACID HAVING A HIGH CONCENTRATION FROM COFFEE CASCARA

(71) Applicant: Anh Quynh Nguyen, Ho Chi Minh (VN)

(72) Inventors: Anh Quynh Nguyen, Ho Chi Minh (VN); Anh Tuan Nguyen, Lam Dong (VN); Ly Thi Phi Trinh, Ho Chi Minh (VN); Vinh Duong Hoang Nguyen, Ho Chi Minh (VN); Trang Nguyen Phuong Huynh, Ho Chi Minh (VN); Thao Thi Thanh Nguyen, Ho Chi Minh (VN); Hai Hoang Ho, Ho Chi Minh (VN)

(73) Assignees: Khai Minh Viet Enzyme Technology JSC, Ho Chi Minh (VN); Viet Thao Nhien Company Limited, Bao Loc (VN)

( * ) Notice: Subject to any disclaimer, the term of this patent is extended or adjusted under 35 U.S.C. 154(b) by 0 days.

(21) Appl. No.: 18/415,597

(22) Filed: Jan. 17, 2024

(51) Int. Cl.
 A23F 3/14 (2006.01)
 A23L 27/10 (2016.01)
 A23L 33/135 (2016.01)
 A23L 33/18 (2016.01)
 C12N 9/24 (2006.01)
 C12N 9/42 (2006.01)
 C12P 7/42 (2006.01)

(52) U.S. Cl.
 CPC ............... *A23F 3/14* (2013.01); *A23L 27/10* (2016.08); *A23L 33/135* (2016.08); *A23L 33/18* (2016.08); *C12N 9/2402* (2013.01); *C12N 9/2437* (2013.01); *C12P 7/42* (2013.01); *C12Y 302/01004* (2013.01); *C12Y 302/01015* (2013.01)

(58) Field of Classification Search
 CPC ...................................... A23F 5/00; A23F 3/14
 See application file for complete search history.

(56) References Cited

U.S. PATENT DOCUMENTS

2024/0065297 A1\* 2/2024 Zhang ..................... A23L 2/52

\* cited by examiner

*Primary Examiner* — Tekchand Saidha

(57) ABSTRACT

A method for producing the preparation containing protocatechuic acid (PCA), chlorogenic acid (CGA) and caffeic acid (CA) having a high concentration from coffee cascara comprising: (i) preparing materials; (ii) mixing the coffee cascara ingredient with the sweetener ingredient, and the water ingredient, and then sterilizing to obtain a foundation mixture; (iii) admixing the composition of complex enzyme-probiotic with the foundation mixture, then hydrolyzing to obtain a hydrolyzed mixture; (iv) admixing the composition of complex enzyme-probiotic with the hydrolyzed mixture, then fermenting to obtain a fermented mixture; (v) filtering the fermented mixture for removing the solid part, and collecting the liquid part is a fermented solution; and (vi) concentrating the fermented solution to obtain a preparation containing PCA, CGA and CA having a high concentration from coffee cascara.

15 Claims, 1 Drawing Sheet
Specification includes a Sequence Listing.

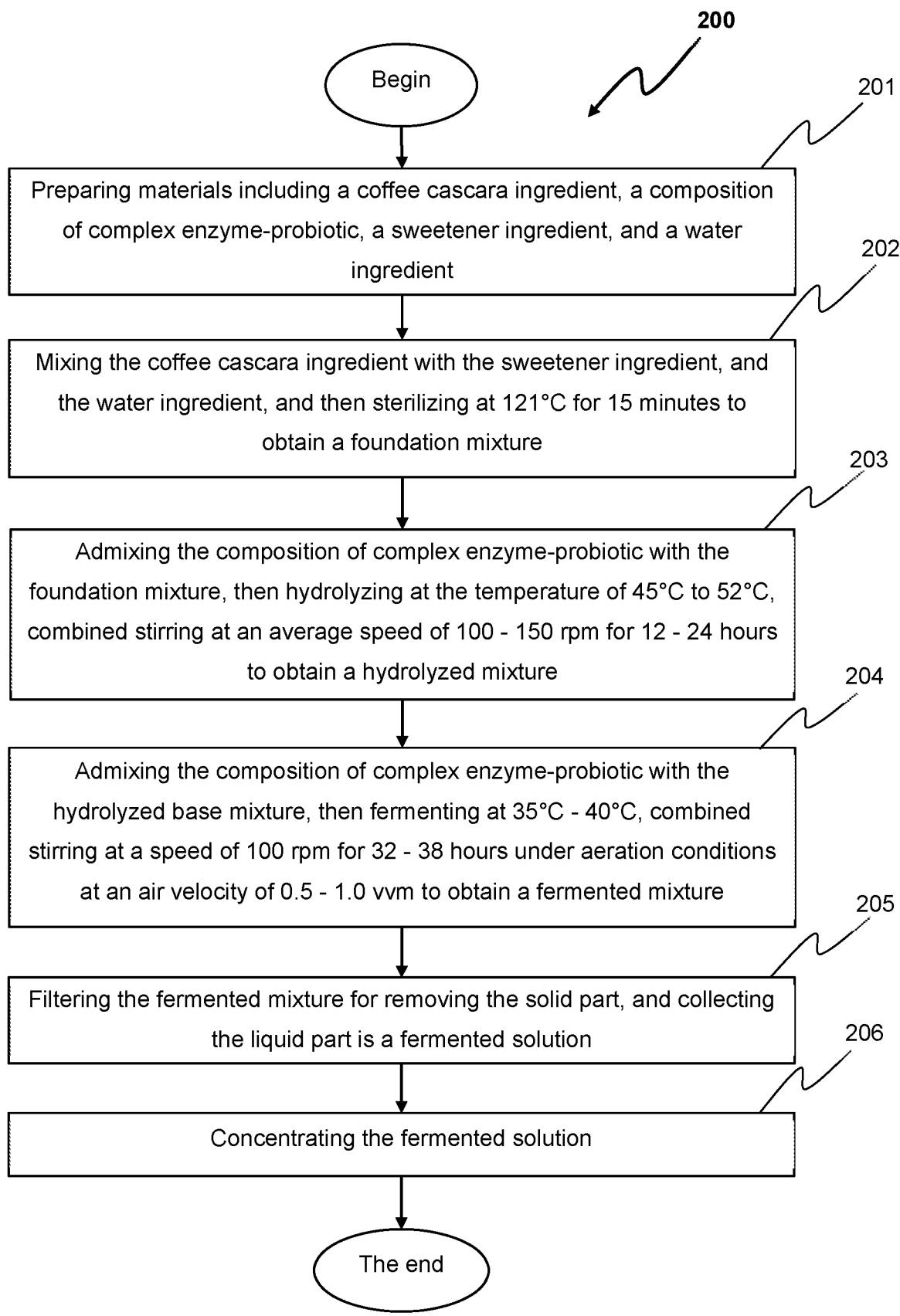

COMPOSITION OF COMPLEX ENZYME-PROBIOTIC AND ITS APPLICATIONS INTO A METHOD FOR PRODUCING A PREPARATION CONTAINING CHLOROGENIC ACID, PROTOCATECHUIC ACID, AND CAFFEIC ACID HAVING A HIGH CONCENTRATION FROM COFFEE CASCARA

FIELD OF THE INVENTION

The present invention relates to a method of producing phenolic compounds from coffee cascara using enzyme-probiotic technology. More specifically, the present invention relates to a composition of complex enzyme-probiotic and its applications into a method for producing the preparation containing protocatechuic acid (PCA), chlorogenic acid (CGA) and caffeic acid (CA) having a high concentration from coffee cascara.

BACKGROUND ART

Coffee stands out as one of the most widely enjoyed beverages globally. While coffee plants thrive in tropical regions, the consumption of this beloved beverage is particularly prevalent in Europe and the United States. Consequently, the international coffee market is predominantly shaped by two main varieties: Arabica coffee (*Coffea arabica*) and Robusta coffee (*Coffea canephora*).

Traditionally, coffee cascara has been considered biodegradable waste, and without proper management, it poses a risk of accumulating and causing severe environmental issues. However, in recent years, researchers worldwide have shown significant interest in innovating and developing processes to convert these by-products into valuable commodities.

Coffee cascara, encompassing husks and pulps, has found applications in beverages like teas and food ingredients. This is attributed to its substantial content of high-value components, including protein, fiber, polysaccharides, taste-enhancing compounds, and even chemicals with a high caloric value.

Notably, key bioactive phenolic compounds are predominantly found in coffee cascara, with protocatechuic acid (PCA), chlorogenic acid (CGA) and caffeic acid (CA) holding particular prominence. These constituents have garnered extensive research attention due to their demonstrated health benefits, including antioxidant, anticarcinogenic, anti-inflammatory, and anti-hypoglycemic properties. These advantages underscore the substantial potential of coffee cascara as a valuable source of health-improving components, in addition to its nutritional aspects.

The extraction process is a critical stage in the recovery of phenolic compounds from plant materials, directly influencing the yield and quality of bioactive compounds. Traditional methods such as solvent and refluxing extraction, while easy to set up, often incur higher costs related to personnel, solvent usage, targeted component loss, and low extraction yields. Modern techniques like ultrasound-assisted and microwave-assisted extraction can overcome these challenges but require more expensive and sophisticated equipment.

Enzymatic hydrolysis has emerged as a promising and environmentally friendly technique for effectively releasing bound bioactive compounds through the degradation of cell wall structures, resulting in an improved extraction yield. The enzyme-assisted process, recognized as an efficient green technique, offers natural bioactive ingredients that align with the requirements of the food and pharmaceutical industries.

Until now, not many reports have focused on producing chlorogenic acid (CGA), protocatechuic acid (PCA), and caffeic acid (CA) from coffee cascara, especially deploying enzyme-assisted extraction as a pretreatment method, probably due to the difficult breakdown structure of coffee cascara. Depending on its structure and chemical component, one needs to find suitable enzymes with high capability to hydrolyze chemical links inside the cascara's structure. Almost all success cases that can apply in industrial production scales have originated from screening and selecting specialized microorganisms for those specific biomass types.

Therefore, it is necessary to isolate bacteria and yeasts efficiently capable of producing tailored enzymes to hydrolyze coffee cascara's non-carbohydrate and carbohydrate structures. This process can facilitate the release of targeted bioactive compounds (CGA, PCA, and CA) from coffee cascara through enzymatic and fermentation processes.

Furthermore, it is necessary to a composition of complex enzyme-probiotic obtained from the process of forming a homogenous solution by mixing an in-house produced enzyme ingredients with a selected probiotic microorganism ingredients, a mineral ingredients, glycerol, and a water ingredient. This composition can create favorable conditions for releasing target bioactive compounds, including protocatechuic acid (PCA), chlorogenic acid (CGA) and caffeic acid (CA), from coffee cascara through enzymatic and fermentation processes.

Furthermore, it is necessary to create a method for producing the preparation containing protocatechuic acid (PCA), chlorogenic acid (CGA) and caffeic acid (CA) having a high concentration from coffee cascara comprising: (i) preparing materials; (ii) mixing the coffee cascara ingredient with the sweetener ingredient, and the water ingredient, and then sterilizing to obtain a foundation mixture; (iii) admixing the composition of complex enzyme-probiotic with the foundation mixture, then hydrolyzing to obtain a hydrolyzed mixture; (iv) admixing the composition of complex enzyme-probiotic with the hydrolyzed mixture, then fermenting to obtain a fermented mixture; (v) filtering the fermented mixture for removing the solid part, and collecting the liquid part is a fermented solution; and (vi) concentrating the fermented solution to obtain a preparation containing PCA, CGA and CA having a high concentration from coffee cascara.

Finally, what is needed to provide the high-quality complex enzyme-probiotic and the method for producing the preparation containing protocatechuic acid (PCA), chlorogenic acid (CGA) and caffeic acid (CA) having a high concentration from coffee cascara that offers simplified steps, optimized technical specifications, and the potential for industrial-scale application.

This invention provides solutions to achieve the above goals.

SUMMARY OF THE INVENTION

Accordingly, an objective of the present invention is to provide a composition of complex enzyme-probiotic obtained from the process of forming a homogenous solution by mixing 25%-35% by volume of an in-house produced enzyme ingredients with 45%-55% by volume of a selected probiotic microorganism ingredients, 3%-7% by volume of a mineral ingredients, 8%-12% by volume of glycerol, and a water ingredient with at a speed of 480 rpm for 30 minutes;

wherein the selected probiotic microorganism ingredients comprising *Lactobacillus plantarum* LV-1 having at least $1\times10^9$ CFU/mL, *Lactobacillus casei* LV-1 having at least $1\times10^9$ CFU/mL, *Lactobacillus paracasei* LV-1 having at least $1\times10^9$ CFU/mL, and *Saccharomyces cerevisiae* LV-1 having at least $1\times10^7$ CFU/mL;

wherein the mineral ingredients comprising sodium chloride (NaCl) having 2.0-4.5 g/L, magnesium sulfate ($MgSO_4$) having 2.0-4.5 g/L, calcium chloride ($CaCl_2$)) having 1.00-2.25 g/L, manganese sulfate ($MnSO_4$) having 0.01-0.1 g/L, and dipotassium hydrogen phosphate ($K_2HPO_4$) having 0.1-2.0 g/L;

wherein the in-house produced enzyme ingredients obtained by mixing a first enzyme solution with a second enzyme solution, and a third enzyme solution; wherein a mixing ratio of the first enzyme solution, the second enzyme solution, and third enzyme solution is (3-5):(1-2):(1-3);

the first enzyme solution obtained by performing in a specific order from (a) to (e) comprising:
 (a) culturing *Lactobacillus plantarum* LV-1 bp inoculating a single colony into the nutrient broth, and then incubation at 30° C.-40° C. for 24-48 hours to obtain a first fermentation solution;
 (b) mixing the first fermentation solution with a citrate buffer solution in a ratio of 1:(1-4), stirring at 150-300 rpm for 30-60 minutes at 30° C.-40° C. to obtain a first temporary mixture; wherein the citrate buffer solution has concentration of 20-50 mM, and pH 4.5-6.5;
 (c) centrifuging the first temporary mixture at 10,000×g at 4° C. for 30-60 minutes, collecting the supernatant to obtain a first extracellular solution;
 (d) filtering the first extracellular solution through membrane filter with a pore size of 0.2 μm to obtain a first filtered extracellular solution; and
 (e) filtering the first filtered extracellular solution using a tangential flow filter with a membrane size of 10 kDa to obtain the first enzyme solution;

the second enzyme solution obtained by performing in a specific order from (a') to (e') comprising:
 (a') culturing *Bacillus subtilis* LV-1 by inoculating a single colony into the nutrient broth, and then incubation at 35° C.-42° C. for 24-48 hours to obtain a second fermentation broth;
 (b') mixing the second fermentation broth with a citrate buffer solution in a ratio of 1:(1-4), stirring at 150-300 rpm for 30-60 minutes at 35° C.-42° C. to obtain a second temporary mixture; wherein the citrate buffer solution has concentration of 20-50 mM and pH 5.0-6.5;
 (c') centrifuging the second temporary mixture at 10,000×g at 4° C. for 30-60 minutes, collecting the supernatant to obtain a second extracellular solution;
 (d') filtering the second extracellular solution through membrane filter with a pore size of 0.2 μm to obtain a second filtered extracellular solution; and
 (e') filtering the second filtered extracellular solution using the tangential flow filter with membrane size of 10 kDa to obtain the second enzyme solution;

the third enzyme solution obtained by performing in a specific order from (a") to (e") comprising:
 (a") culturing *Saccharomyces cerevisiae* LV-1 by inoculating a single colony into Yeast Peptone Dextrose (YPD), incubating at 30° C.-40° C. for 24-48 hours to obtain a third fermentation broth;
 (b") mixing the third fermentation broth with a citrate buffer solution in a ratio of 1:(1-4), stirring at 150-300 rpm for 30-60 minutes at 30° C.-40° C. to obtain a third temporary mixture; wherein the citrate buffer solution has concentration of 20-50 mM and pH 5.0-6.5;
 (c") centrifuging the third temporary mixture at 10,000×g at 4° C. for 30-60 minutes, collecting the supernatant to obtain a third extracellular solution;
 (d") filtering the third extracellular solution through membrane filter with a pore size of 0.2 μm to obtain a filtered third extracellular solution; and
 (e") filtering the third filtered extracellular solution using the tangential flow filter with membrane size of 10 kDa to obtain the third enzyme solution.

Furthermore, the purpose of the invention is to provide A method for producing the preparation containing protocatechuic acid (PCA), chlorogenic acid (CGA) and caffeic acid (CA) having a high concentration from coffee cascara comprising steps performed in the following specific order:
 (i) preparing materials including: a coffee cascara ingredient, a composition of complex enzyme-probiotic, a sweetener ingredient, and a water ingredient;
   wherein the sweetener ingredient is a group of soluble sugars, or a group of mixed natural sweeteners;
   the group of soluble sugars including monosaccharides, and disaccharides;
   the group of mixed natural sweeteners including invert sugar, hydrolyzed sugar from starch, honey, and jaggery;
   in which, prepare the coffee cascara ingredient by performing in a specific order from (A) to (C) comprising:
    (A) selecting a coffee fruits with a pH having 4-5, and brix having 9-15° Bx; wherein the coffee fruits is selected from the species group consisting of *Arabica* coffee (*Coffea arabica* L), *Robusta* coffee (*Coffea canephora*), Liberia coffee (*Coffea excelsa*), and combinations thereof;
    (B) grinding the coffee fruit, then removing the bean to obtain a coffee cascara; and
    (C) drying the coffee cascara at 40-50° C. until reaching a moisture content of 5%-8% to obtain the coffee cascara ingredient; wherein the coffee cascara ingredient containing chemical components includes PCA having at least 3.5 mg/100 g, CGA having at least 30 mg/100 g, and CA having at least 0.25 mg/100 g;
   in which, prepare the composition of complex enzyme-probiotic by mixing an in-house produced enzyme ingredients with a selected probiotic microorganism ingredients, a mineral ingredients, glycerol, and the water ingredient with at a speed of 200-480 rpm for 10-30 minutes;
   in which, prepare the selected probiotic microorganism ingredients by mixing *Lactobacillus plantarum* LV-1 having at least $1\times10^9$ CFU/mL, *Lactobacillus casei* LV-1 having at least $1\times10^9$ CFU/mL, *Lactobacillus paracasei* LV-1 having at least $1\times10^9$ CFU/mL, and *Saccharomyces cerevisiae* LV-1 having at least $1\times10^7$ CFU/mL;
   in which, prepare the mineral ingredients comprising sodium chloride (NaCl) having 2.0-4.5 g/L, magnesium sulfate ($MgSO_4$) having 2.0-4.5 g/L, calcium chloride ($CaCl_2$)) having 1.00-2.25 g/L, manganese sulfate (MnSO$_4$) having 0.01-0.1 g/L, and dipotassium hydrogen phosphate (K$_2$HPO$_4$) having 0.1-2.0 g/L;

in which, prepare the in-house produced enzyme ingredients by mixing a first enzyme solution with a second enzyme solution, and a third enzyme solution; wherein a mixing ratio of the first enzyme solution, the second enzyme solution, and third enzyme solution is (3-5):(1-2):(1-3);

in which, prepare the first enzyme solution by performing in a specific order from (a) to (e) comprising:
  (a) culturing *Lactobacillus plantarum* LV-1 by inoculating a single colony into the nutrient broth, and then incubation at 30° C.-40° C. for 24-48 hours to obtain a first fermentation solution;
  (b) mixing the first fermentation solution with a citrate buffer solution in a ratio of 1:(1-4), stirring at 150-300 rpm for 30-60 minutes at 30° C.-40° C. to obtain a first temporary mixture; wherein the citrate buffer solution has concentration of 20-50 mM, and pH 4.5-6.5;
  (c) centrifuging the first temporary mixture at 10,000×g at 4° C. for 30-60 minutes, collecting the supernatant to obtain a first extracellular solution;
  (d) filtering the first extracellular solution through membrane filter with a pore size of 0.2 μm to obtain a first filtered extracellular solution; and
  (e) filtering the first filtered extracellular solution using a tangential flow filter with a membrane size of 10 kDa to obtain the first enzyme solution;

in which, prepare the second enzyme solution by performing in a specific order from (a') to (e') comprising:
  (a') culturing *Bacillus subtilis* LV-1 by inoculating a single colony into the nutrient broth, and then incubation at 35° C.-42° C. for 24-48 hours to obtain a second fermentation broth;
  (b') mixing the second fermentation broth with a citrate buffer solution in a ratio of 1:(1-4), stirring at 150-300 rpm for 30-60 minutes at 35° C.-42° C. to obtain a second temporary mixture; wherein the citrate buffer solution has concentration of 20-50 mM and pH 5.0-6.5;
  (c') centrifuging the second temporary mixture at 10,000×g at 4° C. for 30-60 minutes, collecting the supernatant to obtain a second extracellular solution;
  (d') filtering the second extracellular solution through membrane filter with a pore size of 0.2 μm to obtain a second filtered extracellular solution; and
  (e') filtering the second filtered extracellular solution using the tangential flow filter with membrane size of 10 kDa to obtain the second enzyme solution;

in which, prepare the third enzyme solution by performing in a specific order from (a") to (e") comprising:
  (a") culturing *Saccharomyces cerevisiae* LV-1 by inoculating a single colony into Yeast Peptone Dextrose (YPD), incubating at 30° C.-40° C. for 24-48 hours to obtain a third fermentation broth;
  (b") mixing the third fermentation broth with a citrate buffer solution in a ratio of 1:(1-4), stirring at 150-300 rpm for 30-60 minutes at 30° C.-40° C. to obtain a third temporary mixture; wherein the citrate buffer solution has concentration of 20-50 mM and pH 5.0-6.5;
  (c") centrifuging the third temporary mixture at 10,000×g at 4° C. for 30-60 minutes, collecting the supernatant to obtain a third extracellular solution;
  (d") filtering the third extracellular solution through membrane filter with a pore size of 0.2 μm to obtain a filtered third extracellular solution; and
  (e") filtering the third filtered extracellular solution using the tangential flow filter with membrane size of 10 kDa to obtain the third enzyme solution.

(ii) mixing the coffee cascara ingredient with the sweetener ingredient, and the water ingredient, and then sterilizing at 121° C. for 15 minutes to obtain a foundation mixture;
  wherein a mixing ratio of the coffee cascara ingredient, the sweetener ingredient, and the water ingredient is (1-2):(1-2):(7-9);

(iii) admixing the composition of complex enzyme-probiotic with the foundation mixture at step (ii), then hydrolyzing at the temperature of 45° C. to 52° C., combined stirring at an average speed of 100-150 rpm for 12-24 hours to obtain a hydrolyzed mixture;
  wherein a mixing ratio of the composition of complex enzyme-probiotic and the base mixture is (1-5): 100;
  wherein the hydrolyzed mixture containing chemical components includes:
    a PCA having a concentration n times higher than the PCA of the coffee cascara ingredient; wherein n>0;
    a CGA having a concentration m times higher than the CGA of the coffee cascara ingredient; wherein m>0; and
    a CA having a concentration k times higher than the CA of the coffee cascara ingredient; wherein k>0;

(iv) admixing the composition of complex enzyme-probiotic with the hydrolyzed base mixture at step (iii), then fermenting at 35° C.-40° C., combined stirring at a speed of 100 rpm for 32-38 hours under aeration conditions at an air velocity of 0.5-1.0 vvm to obtain a fermented mixture;
  wherein a mixing ratio of the composition of complex enzyme-probiotic and the hydrolyzed base mixture is 1:(15-25);
  wherein the fermented mixture containing chemical components includes:
    a PCA having a concentration n times higher than the PCA of the coffee cascara ingredient; wherein n'>n;
    a CGA having a concentration m times higher than the CGA of the coffee cascara ingredient; wherein m'>m; and
    a CA having a concentration k times higher than the CA of the coffee cascara ingredient; wherein k'>k;

(v) filtering the fermented mixture at step (iv) for removing the solid part, and collecting the liquid part is a fermented solution; and (vi) concentrating the fermented solution at step (v) until the brix having 45° Bx-55° Bx to obtain a preparation containing PCA, CGA and CA having a high concentration from coffee cascara.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWING

The accompanying drawings, which are incorporated in and form a part of this specification, illustrate embodiments of the invention and, together with the description, serve to explain the principles of the invention.

FIG. 1 is a flowchart illustrating a method for producing the preparation containing protocatechuic acid (PCA), chlorogenic acid (CGA) and caffeic acid (CA) having a high concentration from coffee cascara 200 according to the embodiment of the present invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

It should be noted that mixing machine/device, centrifuge machine/device, filtering machine/device, fermenter machine/device etc., and other similar machines/devices are well-known in the fields of food processing, biochemistry, and biotechnology. Therefore, detailed descriptions and operating principles of these machines/devices are not provided to avoid obscuring unnecessary aspects of the invention.

It should be noted that the term "coffee cascara" is understood to comprise the husk and pulp of coffee fruit.

The first aspect of the present application relates to a microorganism mixture is preserved at Khai Minh Viet Enzyme Technology Joint Stock Company; wherein the microorganism mixture comprising *Lactobacillus plantarum* LV-1, *Bacillus subtilis* LV-1, *Saccharomyces cerevisiae* LV-1, *Lactobacillus casei* LV-1 and *Lactobacillus paracasei* LV-1.

In the present invention, the strain *Lactobacillus plantarum* LV-1 was isolated from fermented fresh coffee cherries collected in Lam Dong province, Vietnam. When cultured on MRS medium, the colonies exhibited round, white, and nontransparent characteristics, with sizes ranging from pinprick-sized to 2 mm. This bacterium was identified as gram-positive, rod-shaped, non-sporeforming, non-motile, and catalase-negative. The identification of the strain *Lactobacillus plantarum* LV-1 was conducted based on morphological characteristics and the 16S rRNA gene region. The sequencing results of the 16S rRNA gene region using primers 27F (5'-AGAGTTTGATCCTGGCTCAG-3) and 1492R (5'-GGTTACCTTGTTACGACTT-3) are represented in SEQ ID No. 1.

The strain *Lactobacillus plantarum* LV-1 demonstrates the ability to ferment coffee cascara, resulting in an increased concentration of phenolic compounds. This is evidenced through various evaluation parameters, including total phenolic compounds (TPC) and total soluble solids (TSS) concentration. The experiment assesses the effectiveness of coffee cascara fermentation by comparing the strain *Lactobacillus plantarum* LV-1 with the reference strain *Lactobacillus plantarum* ATCC 36858. The detailed experimental results are presented in Table 1.

TABLE 1

TPC and TSS concentration of coffee cascara fermentation by *Lactobacillus plantarum* LV-1 and *Lactobacillus plantarum* ATCC 36858

| Composition | Concentration (g/L) | | | |
|---|---|---|---|---|
| Peptone | 5.5-10.0 | 2.5-5.0 | 0.5-2.0 | 0.1-0.4 |
| Yeast Extract | 1.1-2.0 | 0.5-1.0 | 0.2-0.4 | 0.05-0.15 |
| Coffee cascara | 1-5 | 6-20 | 25-50 | 60-100 |
| TPC (mg/L) | | | | |
| *Lactobacillus plantarum* LV-1 | 236.5-709.6 | 887.3-1865.3 | 2033.1-2948.9 | 2588.4-3085.1 |
| *Lactobacillus plantarum* ATCC 36858 | 23.6-117.6 | 124.8-232.0 | 220.1-358.2 | 325.6-438.3 |
| TSS (° Bx) | | | | |
| *Lactobacillus plantarum* LV-1 | 7.2-9.3 | 7.4-9.6 | 8.01-11.3 | 8.9-13.0 |
| *Lactobacillus plantarum* ATCC 36858 | 4.1-5.0 | 5.3-6.2 | 5.2-6.1 | 5.9-6.2 |

Based on the data in Table 1, the total phenolic compounds (TPC) in the fermented coffee cascara solution using the strain *Lactobacillus plantarum* LV-1 ranged from 236.5 to 3085.1 mg/L, and the total solid soluble (TSS) varied from 7.2 to 13.0° Bx, depending on the amount of coffee cascara added during the fermentation process. In contrast, in the fermented coffee cascara solution using the strain *Lactobacillus plantarum* ATCC 36858, the TPC ranged from 23.6 to 438.3 mg/L, and the TSS changed from 4.1 to 6.2° Bx. *Lactobacillus plantarum* LV-1 demonstrated significantly higher TPC and TSS levels than the well-known strain *Lactobacillus plantarum* ATCC 36858.

In the present invention, the strain *Bacillus subtilis* LV-1 was isolated from fermented fresh coffee cherries collected in Lam Dong province, Vietnam. When cultured on LB medium, the colonies displayed irregular, gray-white, round shapes with opaque, medium-sized, and raised features, sometimes with margins. They exhibited a white and dull appearance with a wet texture. Upon preliminary characterization, it was verified that the cells were rod-like, Gram-positive, mobile, spore-forming under aerobic conditions, and catalase-positive. The strain *Bacillus subtilis* LV-1 was identified based on morphological characteristics and the 16S rRNA gene region. The sequencing results of the 16S rRNA gene region using primers 27F (5'-AGAGTTTGATCCTGGCTCAG-3) and 1492R (5'-GGTTACCTTGTTACGACTT-3) are represented by SEQ ID No. 2.

The strain *Bacillus subtilis* LV-1 has the ability to ferment coffee cascara, leading to an increase in phenolic compound levels. This is demonstrated through evaluation criteria, including total phenolic compounds (TPC) and total soluble solids (TSS) concentrations in the fermentation experiment of coffee cascara with *Bacillus subtilis* LV-1 and *Bacillus* sp. NRRL Y-7124. The experimental results are presented in Table 2.

TABLE 2

TPC and TSS concentration of coffee cascara fermentation by *Bacillus subtilis* LV-1 and *Bacillus* sp. NRRL Y-7124

| Composition | Concentration (g/L) | | | |
|---|---|---|---|---|
| Peptone | 5.5-10.0 | 2.5-5.0 | 0.5-2.0 | 0.1-0.4 |
| Yeast Extract | 1.1-2.0 | 0.5-1.0 | 0.2-0.4 | 0.05-0.15 |
| Coffee cascara | 1-5 | 6-20 | 25-50 | 60-100 |
| TPC (mg/L) | | | | |
| *Bacillus subtilis* LV-1 | 43.4-124.2 | 145.0-441.2 | 394.5-1147.6 | 1301.7-2227.2 |
| *Bacillus* sp. NRRL Y-7124 | 23.2-84.6 | 77.1-186.2 | 157.4-422.1 | 403.2-528.4 |
| TSS (° Bx) | | | | |
| *Bacillus subtilis* LV-1 | 6.1-9.1 | 6.2-8.7 | 6.3-8.8 | 6.4-8.8 |
| *Bacillus* sp. NRRL Y-7124 | 6.3-7.4 | 6.6-7.3 | 6.5-7.2 | 6.3-7.4 |

Based on the data in Table 2, the total phenolic content (TPC) in the fermented coffee cascara solution using *Bacillus subtilis* LV-1 ranges from 43.4 to 2227.2 mg/L, and total soluble solids (TSS) fluctuate from 6.1 to 8.80° Bx, depending on the amount of coffee cascara added during the fermentation process, meanwhile, in the fermented coffee cascara solution with *Bacillus* sp. NRRL Y-7124, TPC varies from 23.2 to 528.4 mg/L, and TSS changes from 6.3 to 7.4° Bx. The strain *Bacillus subtilis* LV-1 demonstrates significantly higher TPC and TSS levels than the well-known strain *Bacillus* sp. NRRL Y-7124.

In the present invention, the strain *Saccharomyces cerevisiae* LV-1 was isolated from fermented fresh coffee cherries collected in Lam Dong province, Vietnam. When grown on YPD agar medium with the addition of 10% ethanol, *Saccharomyces cerevisiae* LV-1 colonies appeared small, with diameters ranging from 2.0 to 4.0 mm after three days of culture. They were round, creamy, or beige-colored patches, composed of millions of individual yeast cells that reproduce asexually through budding. Under a microscope, the individual *Saccharomyces cerevisiae* cells were oval-shaped and typically measured about 3-4 micrometers in diameter. The strain *Saccharomyces cerevisiae* LV-1 was identified based on morphological characteristics and the ITS gene region. The sequencing results of the ITS gene region using primers ITS3 (5'-GCATCGAT-GAAGAACGCAGC-3') and ITS4 (5'-TCCTCCGCTTATT-GATATGC-3') are presented in SEQ ID No. 3.

The strain *Saccharomyces cerevisiae* LV-1 has the capability to ferment coffee cascara, thereby increasing the phenolic compound content. This has been demonstrated through various evaluation parameters, including total phenolic compounds (TPC) and total soluble solids (TSS) concentration in experiments investigating the effectiveness of coffee cascara fermentation by *Saccharomyces cerevisiae* LV-1 and *Saccharomyces cerevisiae* KCTC 7906. The experimental results are presented in Table 3.

TABLE 3

TPC and TSS concentration of coffee cascara fermentation by *Saccharomyces cerevisiae* LV-1 and *Saccharomyces cerevisiae* KCTC 7906

| Composition | Concentration (g/L) | | | |
|---|---|---|---|---|
| Peptone | 5.5-10.0 | 2.5-5.0 | 0.5-2.0 | 0.1-0.4 |
| Yeast Extract | 1.1-2.0 | 0.5-1.0 | 0.2-0.4 | 0.05-0.15 |
| Coffee cascara | 1-5 | 6-20 | 25-50 | 60-100 |
| TPC (mg/L) | | | | |
| *Saccharomyces cerevisiae* LV-1 | 45.6-216.4 | 302.4-835.3 | 1002.1-1556.0 | 1339.0-2280.8 |
| *Saccharomyces cerevisiae* KCTC 7906 | 34.5-172.2 | 155.4-232.1 | 204.5-290.4 | 266.4-433.9 |
| TSS (°Bx) | | | | |
| *Saccharomyces cerevisiae* LV-1 | 6.1-8.7 | 6.2-8.3 | 5.3-7.7 | 4.8-7.5 |
| *Saccharomyces cerevisiae* KCTC 7906 | 5.3-6.2 | 4.8-5.5 | 5.3-5.9 | 4.4-5.1 |

Based on the data in Table 3, the total phenolic content (TPC) in the fermented coffee cascara solution using the strain *Saccharomyces cerevisiae* LV-1 ranged from 45.6 to 2280.8 mg/L, and the total soluble solids (TSS) varied from 4.8 to 8.7° Bx, depending on the amount of coffee cascara added during fermentation. In comparison, in the fermented coffee cascara solution using the strain *Saccharomyces cerevisiae* KCTC 7906, TPC ranged from 34.5 to 433.9 mg/L, and TSS varied from 4.4 to 6.2° Bx. The strain *Saccharomyces cerevisiae* LV-1 exhibited significantly higher TPC and TSS levels compared to the well-known strain *Saccharomyces cerevisiae* KCTC 7906.

In the present invention, the strains *Lactobacillus casei* LV-1 and *Lactobacillus paracasei* LV-1 were isolated from fermented fresh coffee cherries collected in Lam Dong province, Vietnam. The colonies of *Lactobacillus casei* LV-1 and *Lactobacillus paracasei* LV-1 are cultured on MRS medium, exhibiting round shapes, white color, and non-transparency, with sizes ranging from 0.5 to 2 mm. These bacteria are characterized as Gram-positive, rod-shaped, non-sporeforming, non-motile, and catalase-negative. The identification of the strains *Lactobacillus casei* LV-1 and *Lactobacillus paracasei* LV-1 was conducted based on morphological characteristics and the 16S rRNA gene region. The strains *Lactobacillus casei* LV-1 and *Lactobacillus paracasei* LV-1 were sequenced in the 16S rRNA gene region using primers 27F (5'-AGAGTTT-GATCCTGGCTCAG-3) and 1492R (5'-GGTTACCTTGT-TACGACTT-3). The sequencing results for the 16S rRNA gene region of *Lactobacillus casei* LV-1 and *Lactobacillus paracasei* LV-1 are presented in SEQ ID No. 4 and SEQ ID No. 5, respectively.

The strains *Lactobacillus casei* LV-1 and *Lactobacillus paracasei* LV-1 have the ability to ferment coffee cascara, leading to an increase in the content of phenolic compounds. This is demonstrated based on evaluation criteria, including total phenolic compounds (TPC), protocatechuic acid (PCA), chlorogenic acid (CGA) and caffeic acid (CA) in the experiment investigating the efficiency of coffee cascara fermentation, as listed in Table 4 below.

TABLE 4

TPC, PCA, CGA and CA concentrations of coffee cascara
fermentation by Lactobacillus casei LV-1 and
Lactobacillus paracasei LV-1

| Experimental conditions | Phenolic compounds | | | |
|---|---|---|---|---|
| | TPC (mg/L) | PCA (mg/100 g) | CGA (mg/100 g) | CA (mg/100 g) |
| Lactobacillus casei LV-1 | 225.4-432.2 | 18.9-33.5 | 103.5-245.3 | 10.3-23.2 |
| Lactobacillus paracasei LV-1 | 201.9-464.4 | 20.1-36.2 | 98.5-242.1 | 11.4-26.2 |

The second aspect of the present application relates to a composition of complex enzyme-probiotic 100 ("composition 100") obtained from the process of forming a homogenous solution by mixing 25%-35% by volume of an in-house produced enzyme ingredients with 45%-55% by volume of a selected probiotic microorganism ingredients, 3%-7% by volume of a mineral ingredients, 8%-12% by volume of glycerol, and a water ingredient with at a speed of 480 rpm for 30 minutes.

According to the preferred embodiment of the present invention, the composition comprising: the in-house produced enzyme ingredients having 30% by volume; the selected probiotic microorganism ingredients having 50% by volume; the mineral ingredients having 5% by volume; the glycerol having 10% by volume; and the remainder is the water.

In the present invention, the selected probiotic microorganism ingredients comprising Lactobacillus plantarum LV-1 having at least $1 \times 10^9$ CFU/mL, Lactobacillus casei LV-1 having at least $1 \times 10^9$ CFU/mL, Lactobacillus paracasei LV-1 having at least $1 \times 10^9$ CFU/mL, and Saccharomyces cerevisiae LV-1 having at least $1 \times 10^7$ CFU/mL.

Referring to Table 5 below, it can be observed that the fermentation efficiency of coffee cascara by the selected probiotic microorganism ingredients as well as their combination, surpasses that of other commercial microbial strains such as Lactobacillus plantarum ATCC 36858, Saccharomyces cerevisiae KCTC 7906, and Bacillus sp. NRRL Y-7124. Specifically, the values of total phenolic compounds (TPC), protocatechuic acid (PCA), chlorogenic acid (CGA), and caffeic acid (CA) are significantly higher. The strain Saccharomyces cerevisiae LV-1 and the selected probiotic microorganism ingredients condition are significantly higher compared to commercial strains.

TABLE 5

Changes in TPC, PCA, CGA, and CA obtained in the fermentation
broth during the fermentation of coffee cascara
by the investigated microbial strains

| Experimental conditions | Phenolic compounds | | | |
|---|---|---|---|---|
| | TPC (mg/L) | PCA (mg/100 g) | CGA (mg/100 g) | CA (mg/100 g) |
| Control | 44.6-146.5 | 5.6-19.5 | 20.4-80.5 | 4.2-6.2 |
| Lactobacillus plantarum ATCC 36858 | 89.4-257.6 | 12.1-35.3 | 33.5-123.2 | 5.7-15.6 |
| Saccharomyces cerevisiae KCTC 7906 | 102.4-223.4 | 10.2-32.1 | 39.4-121.4 | 4.5-12.4 |
| Bacillus sp. NRRL Y-7124 | 98.4-234.2 | 12.2-33.4 | 42.1-125.2 | 4.5-13.2 |
| Lactobacillus plantarum LV-1 | 259.9-1453.4 | 20.1-42.1 | 132.2-345.4 | 10.3-23.4 |
| Lactobacillus casei LV-1 | 407.3-1432.2 | 10.3-33.5 | 66.8-245.2 | 10.6-23.2 |
| Lactobacillus paracasei LV-1 | 238.0-1464.4 | 20.2-36.2 | 100.1-242.1 | 11.0-26.2 |
| Saccharomyces cerevisiae LV-1 | 337.7-1551.6 | 10.4-35.5 | 89.4-235.6 | 15.9-35.5 |
| The selected probiotic microorganism ingredients | 337.5-1362.2 | 12.3-32.4 | 100.4-262.4 | 22.6-42.3 | in which: control condition means that the condition without microorganisms.

In the present invention, the mineral ingredients comprising sodium chloride (NaCl) having 2.0-4.5 g/L, magnesium sulfate ($MgSO_4$) having 2.0-4.5 g/L, calcium chloride ($CaCl_2$)) having 1.00-2.25 g/L, manganese sulfate ($MnSO_4$) having 0.01-0.1 g/L, and dipotassium hydrogen phosphate ($K_2HPO_4$) having 0.1-2.0 g/L.

In the present invention, the in-house produced enzyme ingredients obtained by mixing a first enzyme solution with a second enzyme solution, and a third enzyme solution; wherein a mixing ratio of the first enzyme solution, the second enzyme solution, and third enzyme solution is (3-5):(1-2):(1-3).

According to the preferred embodiment of the present invention, the mixing ratio of the first enzyme solution, the second enzyme solution, and third enzyme solution is 5:2:3.

In the present invention, the in-house produced enzyme ingredients including endoglucanase having 1,500-10,000 U/g protein, polygalacturonase having 1,000-5,500 U/g protein, and amyloglucosidase having 930-5,500 U/g protein.

According to the preferred embodiment of the present invention, the in-house produced enzyme ingredients including endoglucanase having 5,000-10,000 U/g protein, polygalacturonase having 3,000-5,500 U/g protein, and amyloglucosidase having 3,000-5,500 U/g protein.

In the present invention, the first enzyme solution obtained by performing in a specific order from (a) to (e) comprising:
  (a) culturing Lactobacillus plantarum LV-1 by inoculating a single colony into the nutrient broth, and then incubation at 30° C.-40° C. for 24-48 hours to obtain a first fermentation solution;
  (b) mixing the first fermentation solution with a citrate buffer solution in a ratio of 1:(1-4), stirring at 150-300 rpm for 30-60 minutes at 30° C.-40° C. to obtain a first temporary mixture; wherein the citrate buffer solution has concentration of 20-50 mM, and pH 4.5-6.5;
  (c) centrifuging the first temporary mixture at 10,000×g at 4° C. for 30-60 minutes, collecting the supernatant to obtain a first extracellular solution;
  (d) filtering the first extracellular solution through membrane filter with a pore size of 0.2 µm to obtain a first filtered extracellular solution; and (e) filtering the first filtered extracellular solution using a tangential flow filter with a membrane size of 10 kDa to obtain the first enzyme solution;

In the present invention, the second enzyme solution obtained by performing in a specific order from (a') to (e') comprising:

(a') culturing *Bacillus subtilis* LV-1 by inoculating a single colony into the nutrient broth, and then incubation at 35° C.-42° C. for 24-48 hours to obtain a second fermentation broth;

(b') mixing the second fermentation broth with a citrate buffer solution in a ratio of 1:(1-4), stirring at 150-300 rpm for 30-60 minutes at 35° C.-42° C. to obtain a second temporary mixture; wherein the citrate buffer solution has concentration of 20-50 mM and pH 5.0-6.5;

(c') centrifuging the second temporary mixture at 10,000×g at 4° C. for 30-60 minutes, collecting the supernatant to obtain a second extracellular solution;

(d') filtering the second extracellular solution through membrane filter with a pore size of 0.2 µm to obtain a second filtered extracellular solution; and (e') filtering the second filtered extracellular solution using the tangential flow filter with membrane size of 10 kDa to obtain the second enzyme solution;

In the present invention, the third enzyme solution obtained by performing in a specific order from (a") to (e") comprising:

(a") culturing *Saccharomyces cerevisiae* LV-1 by inoculating a single colony into Yeast Peptone Dextrose (YPD), incubating at 30° C.-40° C. for 24-48 hours to obtain a third fermentation broth;

(b") mixing the third fermentation broth with a citrate buffer solution in a ratio of 1:(1-4), stirring at 150-300 rpm for 30-60 minutes at 30° C.-40° C. to obtain a third temporary mixture; wherein the citrate buffer solution has concentration of 20-50 mM and pH 5.0-6.5:

(c") centrifuging the third temporary mixture at 10,000×g at 4° C. for 30-60 minutes, collecting the supernatant to obtain a third extracellular solution;

(d") filtering the third extracellular solution through membrane filter with a pore size of 0.2 µm to obtain a filtered third extracellular solution; and (e") filtering the third filtered extracellular solution using the tangential flow filter with membrane size of 10 kDa to obtain the third enzyme solution.

The hydrolysis efficiency of coffee cascara by the in-house produced enzyme ingredients is superior to that of commercial enzymes, including Cellulast, Viscozyme, and Pectinex. This is demonstrated based on evaluation criteria, including protocatechuic acid (PCA), chlorogenic acid (CGA), and caffeic acid (CA), in the experiment assessing the hydrolysis efficiency of coffee cascara by the enzyme component and commercial enzymes. The experimental results are presented in Table 6.

TABLE 6

Content of phenolic compounds according to different hydrolytic enzymes

| Enzymes | Phenolic compounds | | |
|---|---|---|---|
| | PCA (mg/100 g) | CGA (mg/100 g) | CA (mg/100 g) |
| Cellulast | 33.5-74.7 | 100.2-230.0 | 13.2-32.4 |
| Pectinex | 23.1-43.7 | 94.3-197.3 | 13.2-33.5 |
| Viscozyme | 25.2-50.6 | 123.7-209.6 | 12.0-22.8 |
| The in-house produced enzyme ingredients | 59.1-203.9 | 312.4-497.3 | 35.6-95.6 |

Based on the data in Table 6, it can be observed that the in-house produced enzyme ingredients have shown significantly higher performance in the hydrolysis of coffee cascara compared to other commercial enzymes. For protocatechuic acid (PCA), the content reached 203.9 mg/100 g, much higher than Cellulast (74.7 mg/100 g), Pectinex (43.7 mg/100 g), and Viscozyme (50.6 mg/100 g). Regarding chlorogenic acid (CGA), the in-house produced enzyme ingredients demonstrated a remarkable superiority with a content of up to 497.3 mg/100 g, while Cellulast achieved 230.0 mg/100 g, Pectinex had 197.3 mg/100 g, and Viscozyme reached 209.6 mg/100 g. Additionally, for caffeic acid (CA), the content of 95.6 mg/100 g in the enzyme component is also much higher than Cellulast (32.4 mg/100 g), Pectinex (33.5 mg/100 g), and Viscozyme (22.8 mg/100 g).

Evaluating the effectiveness of the composition 100 involves increasing the concentration of chemical components, including protocatechuic acid (PCA), chlorogenic acid (CGA), and caffeic acid, through the combined hydrolysis stage using the in-house produced enzyme ingredients and fermentation stage using the selected probiotic microorganism ingredients of the coffee cascara. This is demonstrated based on evaluation criteria including total phenolic compounds (TPC), protocatechuic acid (PCA), chlorogenic acid (CGA), and caffeic acid (CA), in the experiment assessing the effectiveness of combining the in-house produced enzyme ingredients with the selected probiotic microorganism ingredients during the fermentation of coffee cascara. The results of the experiment are presented in Table 7.

TABLE 7

Results of the experiment assessing the effectiveness of combining the in-house produced enzyme ingredients with the selected probiotic microorganism ingredients during the fermentation of coffee cascara

| Experimental conditions | Phenolic compounds | | | |
|---|---|---|---|---|
| | TPC (mg/L) | PCA (mg/100 g) | CGA (mg/100 g) | CA (mg/100 g) |
| 1 | 223.1-654.5 | 33.2-103.9 | 55.4-197.3 | 23.5-55.6 |
| 2 | 235.7-1021.5 | 29.4-212.1 | 339.2-1022.5 | 34.5-84.2 |
| 3 | 156.7-828.3 | 35.6-182.6 | 274.5-981.3 | 30.1-88.1 |
| 4 | 202.6-882.3 | 47.2-185.3 | 391.4-988.5 | 26.5-88.9 |
| 5 | 561.3-1915.1 | 74.2-197.1 | 501.3-1492.0 | 34.3-91.0 |
| 6 | 409.4-1882.3 | 122.4-284.9 | 499.2-1518.4 | 34.7-88.5 |
| 7 | 449.6-2083.2 | 49.5-189.6 | 305.6-1439.7 | 41.2-138.1 |
| 8 | 503.2-1976.5 | 102.3-234.6 | 422.4-1387.5 | 33.5-132.0 |
| 9 | 704.4-2182.3 | 112.4-285.3 | 392.3-1698.7 | 40.1-128.1 | in which: condition 1: hydrolysis by the in-house produced enzyme ingredients;

condition 2: hydrolysis by the in-house produced enzyme ingredients and fermentation by *Lactobacillus plantarum* ATCC 36858;

condition 3: hydrolysis by the in-house produced enzyme ingredients and fermentation by *Saccharomyces cerevisiae* KCTC 7906;

condition 4: hydrolysis by the in-house produced enzyme ingredients and fermentation by *Bacillus* sp. NRRL Y-7124;

condition 5: hydrolysis by the in-house produced enzyme ingredients and fermentation by *Lactobacillus plantarum* LV-1;

condition 6: hydrolysis by the in-house produced enzyme ingredients and fermentation by *Lactobacillus casei* LV-1;

condition 7: hydrolysis by the in-house produced enzyme ingredients and fermentation by *Lactobacillus paracasei* LV-1;

condition 8: hydrolysis by the in-house produced enzyme ingredients and fermentation by *Saccharomyces cerevisiae* LV-1; and condition 9: hydrolysis by the in-house produced enzyme ingredients and fermentation by the selected probiotic microorganism ingredients.

Based on the data in Table 7, it can be observed that compared to the condition 1 without microbial inoculation, the conditions from 2 to 9 significantly enhanced the values of total phenolic compounds (TPC), protocatechuic acid (PCA), chlorogenic acid (CGA), and caffeic acid (CA). Particularly, the condition 9, involving hydrolysis and fermentation by Composition 100, exhibited the highest increase in phenolic compounds, with TPC reaching a value of 2182.3 mg/L, PCA at 285.3 mg/100 g, CGA at 1698.7 mg/100 g, and CA at 128.1 mg/100 g.

The third aspect of the present application relates to a method for producing the preparation containing protocatechuic acid (PCA), chlorogenic acid (CGA) and caffeic acid (CA) having a high concentration from coffee cascara 200 ("method 200"). Referring to FIG. 1, method 200 begins with at step 201 preparing materials including: a coffee cascara ingredient, the composition 100, a sweetener ingredient, and a water ingredient.

In the present invention, prepare the coffee cascara ingredient by performing in a specific order from (A) to (C) comprising:

(A) selecting and preparing coffee fruits by a predetermined quality guideline;
wherein said predetermined quality guideline comprises selecting said coffee fruits that have pH of 4-5, and brix of 9-15° Bx; and performing visual inspection of said coffee fruits that exhibit colors such as red, yellow, or deep purple (depending on the coffee variety).
wherein the coffee fruits is selected from the species group consisting of *Arabica* coffee (*Coffea arabica* L), *Robusta* coffee (*Coffea canephora*), Liberia coffee (*Coffea excelsa*), and combinations thereof;

(B) grinding the coffee fruit, then removing the bean to obtain a coffee cascara; and (C) drying the coffee cascara at 40-50° C. until reaching a moisture content of 5%-8% to obtain the coffee cascara ingredient; wherein the coffee cascara ingredient containing chemical components includes PCA having at least 3.5 mg/100 g, CGA having at least 30 mg/100 g, and CA having at least 0.25 mg/100 g.

According to the preferred embodiment of the present invention, the coffee fruits is *Arabica* coffee (*Coffea arabica* L).

In the present invention, the sweetener ingredient is a group of soluble sugars, or a group of mixed natural sweeteners;
the group of soluble sugars including monosaccharides, and disaccharides;
the group of mixed natural sweeteners including invert sugar, hydrolyzed sugar from starch, honey, and jaggery.

According to the preferred embodiment of the present invention, the sweetener ingredient is sugarcane.

In the present invention, the composition 100 has been described above.

At step 202, mixing the coffee cascara ingredient with the sweetener ingredient, and the water ingredient, and then sterilizing at 121° C. for 15 minutes to obtain a foundation mixture.

In the present invention, a mixing ratio of the coffee cascara ingredient, the sweetener ingredient, and the water ingredient is (1-2):(1-2):(7-9).

According to the preferred embodiment of the present invention, the mixing ratio of the coffee cascara ingredient, the sweetener ingredient, and the water ingredient is 1:1:9.

At step 203, admixing the composition of complex enzyme-probiotic with the foundation mixture at step 202, then hydrolyzing at the temperature of 45° C. to 52° C. combined stirring at an average speed of 100-150 rpm for 12-24 hours to obtain a hydrolyzed mixture. It should be noted that the term "admixed/mixed/admixing/mixing" as used in the present invention is understood to mean adding, or reacting, or dissolving homogeneously, or evenly, components in the same solution/mixture.

According to the preferred embodiment of the present invention, hydrolyzing at the temperature of 48° C. to 50° C., combined stirring at an average speed of 120-140 rpm for 16-20 hours.

In the present invention, a mixing ratio of the composition of complex enzyme-probiotic and the base mixture is (1-5):100.

In the present invention, the hydrolyzed mixture containing chemical components includes:
a PCA having a concentration n times higher than the PCA of the coffee cascara ingredient; wherein n>0;
a CGA having a concentration m times higher than the CGA of the coffee cascara ingredient; wherein m>0; and
a CA having a concentration k times higher than the CA of the coffee cascara ingredient; wherein k>0.

According to the preferred embodiment of the present invention, the hydrolyzed mixture containing chemical components includes:
the PCA having a concentration (4-11) times higher than the PCA of the coffee cascara ingredient;
the CGA having a concentration (2-7) times higher than the CGA of the coffee cascara ingredient; and
the CA having a concentration (22-28) times higher than the CA of the coffee cascara ingredient.

At step 204, admixing the composition of complex enzyme-probiotic with the hydrolyzed base mixture at step 203, then fermenting at 35° C.-40° C., combined stirring at a speed of 100 rpm for 32-38 hours under aeration conditions at an air velocity of 0.5-1.0 vvm to obtain a fermented mixture.

According to the preferred embodiment of the present invention, fermenting at 37° C., combined stirring at a speed of 100 rpm for 36 hours under aeration conditions at an air velocity of 0.75 vvm.

In the present invention, a mixing ratio of the composition of complex enzyme-probiotic and the hydrolyzed base mixture is 1:(15-25); more preferably 1:20.

In the present invention, the fermented mixture containing chemical components includes:
- a PCA having a concentration n times higher than the PCA of the coffee cascara ingredient; wherein n'>n;
- a CGA having a concentration m times higher than the CGA of the coffee cascara ingredient; wherein m'>m; and
- a CA having a concentration k times higher than the CA of the coffee cascara ingredient; wherein k'>k.

According to the preferred embodiment of the present invention, the fermented mixture containing chemical components includes:
- the PCA having a concentration (12-18) times higher than the PCA of the coffee cascara ingredient;
- the CGA having a concentration (8-16) times higher than the CGA of the coffee cascara ingredient; and
- the CA having a concentration (75-85) times higher than the CA of the coffee cascara ingredient.

At step 205, filtering the fermented mixture at step 204 for removing the solid part, and collecting the liquid part is a fermented solution.

Finally, at step 206, concentrating the fermented solution at step 205 until the brix having 45° Bx-55° Bx to obtain a preparation containing PCA, CGA and CA having a high concentration from coffee cascara.

According to the preferred embodiment of the present invention, the preparation having 50° Bx.

TABLE 8

Mixed ingredients of the composition 100 according to the embodiment of the present invention

| | | Percentage (%) | | |
|---|---|---|---|---|
| No. | Ingredients | Formula 1 | Formula 2 | Formula 3 |
| 1 | The in-house produced enzyme ingredients | 30 | 35 | 25 |
| 2 | The selected probiotic microorganism ingredients | 50 | 45 | 55 |
| 3 | The mineral ingredients | 5 | 7 | 3 |
| 4 | The glycerol | 10 | 8 | 12 |
| 5 | The water | Remaining percent | Remaining percent | Remaining percent |

Example 1. Method 200 is applied to produce the preparation containing protocatechuic acid (PCA), chlorogenic acid (CGA), and caffeic acid (CA) with a high concentration from 2 kg of coffee cascara obtained from the coffee fruits of *Arabica* coffee (*Coffea arabica* L). Specifically:

(I) preparing materials including: a coffee cascara ingredient, the composition 100, a sugarcane ingredient, and a water ingredient; wherein the coffee cascara ingredient obtained from the coffee fruits of *Arabica* coffee (*Coffea arabica* L);
the coffee cascara ingredient containing chemical components includes PCA having 15.4 mg/100 g, CGA having 126.9 mg/100 g, and CA having 1.6 mg/100 g;
the composition 100 is prepared according to Formula 1 in Table 8;

(II) mixing 2 kg the coffee cascara with 2 kg sugarcane and 18 kg the water, and then sterilizing at 121° C. for 15 minutes to obtain a foundation mixture;

(III) admixing 0.22 kg the composition 100 with the foundation mixture at step (II), then hydrolyzing at 50° C., combined stirring at an average speed of 100 rpm for 12 hours to obtain a hydrolyzed mixture;

(IV) admixing 1.1 kg the composition 100 with the hydrolyzed base mixture at step (III), then fermenting at 37° C., combined stirring at a speed of 100 rpm for 36 hours under aeration conditions at an air velocity of 0.75 vvm to obtain a fermented mixture;

(V) filtering the fermented mixture at step (IV) for removing the solid part, and collecting the liquid part is a fermented solution; and (VI) concentrating the fermented solution at step (V) until the brix having 50° Bx to obtain a preparation containing PCA, CGA and CA having a high concentration from coffee cascara.

Integrate the data of PCA, CGA, and CA of the coffee cascara ingredient to represent the concentration changes in the material (before), after enzymatic (step (III)), and after fermentation (step (IV)), as presented in Table 9 (referenced by FIG. 2).

TABLE 9

Concentration changes of PCA, CGA, and CA in the material (before), after enzymatic, and after fermentation when applying method 200 to coffee cascara obtained from the coffee fruits of Arabica coffee (*Coffea arabica* L).

| Step | Concentration (mg/100 g) | Concentration ratio after enzymatic: before (times) | Concentration ratio after fermentation: before (times) |
|---|---|---|---|
| PCA | | | |
| Before | 13.2 | 10 | 15 |
| After enzymatic | 130.7 | | |
| After fermentation | 202.1 | | |
| CGA | | | |
| Before | 84.9 | 6 | 14 |
| After enzymatic | 523.2 | | |
| After fermentation | 1225.3 | | |
| CA | | | |
| Before | 1.6 | 25 | 80 |
| After enzymatic | 42.3 | | |
| After fermentation | 132.8 | | |

Example 2. Method 200 is applied to produce the preparation containing protocatechuic acid (PCA), chlorogenic acid (CGA), and caffeic acid (CA) with a high concentration from 2 kg of coffee cascara obtained from the coffee fruits of *Robusta* coffee (*Coffea canephora*), following similar steps as in Example 1. Concentration changes of PCA, CGA, and CA in the material (before), after enzymatic, and after fermentation are presented in Table 10.

TABLE 10

Concentration changes of PCA, CGA, and CA in the material (before), after enzymatic, and after fermentation when applying method 200 to coffee cascara obtained from the coffee fruits of Robusta coffee (*Coffea canephora*)

| Step | Concentration (mg/100 g) | Concentration ratio after enzymatic: before (times) | Concentration ratio after fermentation: before (times) |
|---|---|---|---|
| PCA | | | |
| Before | 14.5 | 7 | 12 |
| After enzymatic | 103.8 | | |
| After fermentation | 179.4 | | |
| CGA | | | |
| Before | 116.5 | 5 | 9 |
| After enzymatic | 621.9 | | |
| After fermentation | 1026.1 | | |
| CA | | | |
| Before | 1.0 | 24 | 79 |
| After enzymatic | 24.7 | | |
| After fermentation | 81.3 | | |

Example 3. Method 200 is applied to produce the preparation containing protocatechuic acid (PCA), chlorogenic acid (CGA), and caffeic acid (CA) with a high concentration from 2 kg of coffee cascara obtained from the coffee fruits of Liberia coffee (*Coffea excelsa*), following similar steps as in Example 1. Concentration changes of PCA, CGA, and CA in the material (before), after enzymatic, and after fermentation are presented in Table 11.

TABLE 11

Concentration changes of PCA, CGA, and CA in the material (before), after enzymatic, and after fermentation when applying method 200 to coffee cascara obtained from the coffee fruits of Liberia coffee (*Coffea excelsa*)

| Step | Concentration (mg/100 g) | Concentration ratio after enzymatic: before (times) | Concentration ratio after fermentation: before (times) |
|---|---|---|---|
| PCA | | | |
| Before | 11.2 | 7 | 16 |
| After enzymatic | 83.1 | | |
| After fermentation | 175.2 | | |
| CGA | | | |
| Before | 106.6 | 4 | 10 |
| After enzymatic | 436.4 | | |
| After fermentation | 1045.7 | | |
| CA | | | |
| Before | 1.1 | 26 | 81 |
| After enzymatic | 29.6 | | |
| After fermentation | 92.3 | | |

Example 4. Method 200 is applied to produce the preparation containing protocatechuic acid (PCA), chlorogenic acid (CGA), and caffeic acid (CA) with a high concentration from 2 kg of coffee cascara obtained from the coffee fruits of a mixture of coffee including *Arabica* coffee, *Robusta* coffee and Liberia coffee, following similar steps as in Example 1. Concentration changes of PCA, CGA, and CA in the material (before), after enzymatic, and after fermentation are presented in Table 12.

TABLE 12

Concentration changes of PCA, CGA, and CA in the material (before), after enzymatic, and after fermentation when applying method 200 to coffee cascara obtained from the coffee fruits of a mixture of coffee including Arabica coffee, Robusta coffee and Liberia coffee

| Step | Concentration (mg/100 g) | Concentration ratio after enzymatic: before (times) | Concentration ratio after fermentation: before (times) |
|---|---|---|---|
| PCA | | | |
| Before | 13.7 | 6 | 14 |
| After enzymatic | 83.8 | | |
| After fermentation | 194.2 | | |
| CGA | | | |
| Before | 116.4 | 4 | 8 |
| After enzymatic | 447.0 | | |
| After fermentation | 974.2 | | |
| CA | | | |
| Before | 1.8 | 25 | 80 |
| After enzymatic | 47.0 | | |
| After fermentation | 150.4 | | |

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

Sequences

Included in the present invention are also nucleic acid sequences derived from the nucleotide sequences shown below. The following five gene sequences are disclosed, representing strains of *Lactobacillus plantarum* LV-1 (SEQ ID No. 1), *Bacillus subtilis* LV-1 (SEQ ID No. 2), *Saccharomyces cerevisiae* LV-1 (SEQ ID No. 3), *Lactobacillus casei* LV-1 (SEQ ID No. 4), and *Lactobacillus paracasei* LV-1 (SEQ ID No. 5).

```
                                                          SEQ ID No. 1
CCCTAATCATCTAGTCCCACCTTAAGCGAGCTGAGTTCCTAAAAGAGTTACCCCAC

CGACTTTGGGTGTTACAAACTCTCATGGTGTGACGGGCGGTGTGTACAAGGCCCG

GGAACGTATTCACCGCGGCATGCTGATCCGCGATTACTAGCGATTCCGACTTCAT

GTAGGCGAGTTGCAGCCTACAATCCGAACTGAGAATGGCTTTAAGAGATTAGCTTA

CTCTCGCGAGTTCGCAACTCGTTGTACCATCCATTGTAGCACGTGTGTAGCCCAG

GTCATAAGGGGCATGATGATTTGACGTCATCCCCACCTTCCTCCGGTTTGTCACCG

GCAGTCTCACCAGAGTGCCCAACTTAATGCTGGCAACTGATAATAAGGGTTGCGCT

CGTTGCGGGACTTAACCCAACATCTCACGACACGAGCTGACGACAACCATGCACC

ACCTGTATCCATGTCCCCGAAGGGAACGTCTAATCTCTTAGATTTGCATAGTATGT

CAAGACCTGGTAAGGTTCTTCGCGTAGCTTCGAATTAAACCACATGCTCCACCGCT

TGTGCGGGCCCCCGTCAATTCCTTTGAGTTTCAGCCTTGCGGCCGTACTCCCCAG

GCGGAATGCTTAATGCGTTAGCTGCAGCACTGAAGGGCGGAAACCCTCCAACACT

TAGCATTCATCGTTTACGATATGGACTACCAGGGTATCTAATCCTGTTTGCTACCCA

TACTTTCGAGCCTCAGCGTCAGTTACAGACCAGACAGCCGCCTTCGCCACTGGTG

TTCTTCCATATATCTACGCATTTCACCGCTACACATGGAGTTCCACTGTCCTCTTCT

GCACTCAAGTTTCCCAGTTTCCGATGCACTTCTTCGGTTGAGCCGAAGGCTTTCAC

ATCAGACTTAAAAAACCGCCTGCGCTCGCTTTACGCCCAATAAATCCGGACAACGC

TTGCCACCTACGTATTACCGCGGCTGCTGGCACGTAGTTAGCCGTGGCTTTCTGG

TTAAATACCGTCAATACCTGAACAGTTACTCTCAGATATGTTCTTCTTTAACAACAG

AGTTTTACGAGCCGAAACCCTTCTTCACTCACGCGGCGTTGCTCCATCAGACTTTC

GTCCATTGTGGAAGATTCCCTACTGCTGCCTCCCGTAG.

SEQ ID No. 2
AGAGTTTGATCCTGGCTCAGGACGAACGCTGGCGGCGTGCCTAATACATGCAAGT

CGAGCGGACCGACGGGAGCTTGCTCCCTTAGGTCAGCGGCGGACGGGTGAGTAA

CACGTGGGTAACCTGCCTGTAAGACTGGGATAACTCCGGGAAACCGGGGCTAATA

CCGGATGCTTGATTGAACCGCATGGTTCAATCATAAAAGGTGGCTTTTAGCTACCA

CTTGCAGATGGACCCGCGGCGCATTAGCTAGTTGGTGAGGTAACGGCTCACCAAG

GCGACGATGCGTAGCCGACCTGAGAGGGTGATCGGCCACACTGGGACTGAGACA

CGGCCCAGACTCCTACGGGAGGCAGCAGTAGGGAATCTTCCGCAATGGACGAAA

GTCTGACGGAGCAACGCCGCGTGAGTGATGAAGGTTTTCGGATCGTAAAACTCTG

TTGTTAGGGAAGAACAAGTACCGTTCGAATAGGGCGGTACCTTGACGGTACCTAA

CCAGAAAGCCACGGCTAACTACGTGCCAGCAGCCGCGGTAATACGTAGGTGGCAA

GCGTTGTCCGGAATTATTGGGCGTAAAGCGCGCGCAGGCGGTTTCTTAAGTCTGA
```

-continued

```
TGTGAAAGCCCCCGGCTCAACCGGGGAGGGTCATTGGAAACTGGGGAACTTGAG

TGCAGAAGAGGAGAGTGGAATTCCACGTGTAGCGGTGAAATGCGTAGAGATGTGG

AGGAACACCAGTGGCGAAGGCGACTCTCTGGTCTGTAACTGACGCTGAGGCGCG

AAAGCGTGGGGAGCGAACAGGATTAGATACCCTGGTAGTCCACGCCGTAAACGAT

GAGTGCTAAGTGTTAGAGGGTTTCCGCCCTTTAGTGCTGCAGCAAACGCATTAAGC

ACTCCGCCTGGGGAGTACGGTCGCAAGACTGAAACTCAAAGGAATTGACGGGGG

CCCGCACAAGCGGTGGAGCATGTGGTTTAATTCGAAGCAACGCGAAGAACCTTAC

CAGGTCTTGACATCCTCTGGCAACCCTAGAGATAGGGCTTCCCCTTCGGGGGCAG

AGTGACAGGTGGTGCATGGTTGTCGTCAGCTCGTGTCGTGAGATGTTGGGTTAAG

TCCCGCAACGAGCGCAACCCTTGATCTTAGTTGCCAGCATTCAGTTGGGCACTCTA

AGGTGACTGCCGGTGACAAACCGGAGGAAGGTGGGGATGACGTCAAATCATCATG

CCCCTTATGACCTGGGCTACACACGTGCTACAATGGGCAGAACAAAGGGCAGCGA

AGCCGCGAGGCTAAGCCAATCCCACAAATCTGTTCTCAGTTCGGATCGCAGTCTG

CAACTCGACTGCGTGAAGCTGGAATCGCTAGTAATCGCGGATCAGCATGCCGCGG

TGAATACGTTCCCGGGCCTTGTACACACCGCCCGTCACACCACGAGAGTTTGTAA

CACCCGAAGTCGGTGAGGTAACCTTTTGGAGCCAGCCGCCGAAGGTGGGACAGA

TGATTGGGGTGAAGTCGTAACAAGGTAGCCGTATCGGAAGGTGCGGCTGGATCAC

CTCCTTTCT
```

SEQ ID No. 3
```
AAGAAATTTAATAATTTTGAAAATGGATTTTTTGTTTTGGCAAGAGCATGAGAGCTT

TTACTGGGCAAGAAGACAAGAGATGGAGAGTCCAGCCGGGCCTGCGCTTAAGTGC

GCGGTCTTGCTAGGCTTGTAAGTTTCTTTCTTGCTATTCCAAACGGTGAGAGATTTC

TGTGCTTTTGTTATAGGACAATTAAAACCGTTTCAATACAACACACTGTGGAGTTTT

CATATCTTTGCAACTTTTTCTTTGGGCATTCGAGCAATCGGGGCCCAGAGGTAACA

AACACAAACAATTTTATCTATTCATTAAATTTTTGTCAAAAACAAGAATTTTCGTAACT

GGAAATTTTAAAAATATTAAAAACTTTCAACAACGGATCTCTTGGTTCTCGCATCGA

TGAAGAACGCAGCGAAATGCGATACGTAATGTGAATTGCAGAATTCCGTGAATCAT

CGAATCTTTGAACGCACATTGCCCCCTTGGTATTCCAGGGGGCATGCCTGTTTGAG

CGTCATTTCCTTCTCAAACATTCTGTTTGGTAGTGAGTGATACTCTTTGGAGTTAAC

TTGAAATTGCTGGCCTTTTCATTGGATGTTTTTTTTCCAAAGAGAGGTTTCTCTGCG

TGCTTGAGGTATTTTGCAAGTACGGTCGTTTTAGGTTTTACCAACTGCGGCTAATCT

TTTTTATACTGAGCGTATTGGAACGTTATCGATAAGAAGAGAGCGTGTAGGCAACA

ATGTTCTTAA
```

SEQ ID No. 4
```
GAGAGTTTGATCCTGGCTCAGGACGAACGCTGGCGGCGTGCCTAATACATGCAAG

TCGAACGAACTCTGGTATTGATTGGTGCTTGCATCATGATTTACATTTGAGTGAGTG

GCGAACTGGTGAGTAACACGTGGGAAACCTGCCCAGAAGCGGGGGATAACACCT

GGAAACAGATGCTAATACCGCATAACAACTTGGACCGCATGGTCCGAGTTTGAAAG

ATGGCTTCGGCTATCACTTTTGGATGGTCCCGCGGCGTATTAGCTAGATGGTGAG

GTAACGGCTCACCATGGCAATGATACGTAGCCGACCTGAGAGGGTAATCGGCCAC

ATTGGGACTGAGACACGGCCCAAACTCCTACGGGAGGCAGCAGTAGGGAATCTTC

CACAATGGACGAAAGTCTGATGGAGCAACGCCGCGTGAGTGAAGAAGGGTTTCGG
```

-continued

CTCGTAAAACTCTGTTGTTAAAGAAGAACATATCTGAGAGTAACTGTTCAGGTATTG

ACGGTATTTAACCAGAAAGCCACGGCTAACTACGTGCCAGCAGCCGCGGTAATAC

GTAGGTGGCAAGCGTTGTCCGGATTTATTGGGCGTAAAGCGAGCGCAGGCGGTTT

TTTAAGTCTGATGTGAAAGCCTTATTCTCAACCGAAGAAGTGCATCGGAAACTGGG

AAACTTGAGTGCAGAAGAGGACAGTGGAACTCCATGTGTAGCGGTGAAATGCGTA

GATATATGGAAGAACACCAGTGGCGAAGGCGGCTGTCTGGTCTGTAACTGACGCT

GAGGCTCGAAAGTATGGGTAGCAAACAGGATTAGATACCCTGGTAGTCCATACCG

TAAACGATGAATGCTAAGTGTTGGAGGGTTTCCGCCCTTCAGTGCTGCAGCTAACG

CATTAAGCATTCCGCCTGGGGAGTACGGCCGCAAGGCTGAAACTCAAAGGAATTG

ACGGGGCCCGCACAAGCGGTGGAGCATGTGGTTTAATTCGAAGCTACGCGAAG

AACCTTACCAGGTCTTGACATACTATGCAAATCTAAGAGATTAGACGTTCCCTTCG

GGGACATGGATACAGGTGGTGCATGGTTGTCGTCAGCTCGTGTCGTGAGATGTTG

GGTTAAGTCCCGCAACGAGCGCAACCCTTATTATCAGTTGCCAGCATTAAGTTGGG

CACTCTGGTGAGACTGCCGGTGACAAACCGGAGGAAGGTGGGGATGACGTCAAA

TCATCATGCCCCTTATGACCTGGGCTACACACGTGCTACAATGGATGGTACAACGA

GTTGCGAACTCGCGAGAGTAAGCTAATCTCTTAAAGCCATTCTCAGTTCGGATTGT

AGGCTGCAACTCGCCTACATGAAGTCGGAATCGCTAGTAATCGCGGATCAGCATG

CCGCGGTGAATACGTTCCCGGGCCTTGTACACACCGCCCGTCACACCATGAGAGT

TTGTAACACCCAAAGTCGGTGGGGTAACCTTTTAGGAACCATCGGCCTAAGGTGG

GACAGATGATTAGGGTGAAGTCGTAACAAGGTAGCCGTAGGAGAACCTGCGGCTG

GATCACCTCCT

SEQ ID No. 5

GTTTGATCCTGGCTCAGGACGAACGCTGGCGGCGTGCCTAATACATGCAAGTCGA

ACGAACTCTGGTATTGATTGGTGCTTGCATCATGATTTACATTTGAGTGAGTGGCG

AACTGGTGAGTAACACGTGGGAAACCTGCCCAGAAGCGGGGGATAACACCTGGAA

ACAGATGCTAATACCGCATAACAACTTGGACCGCATGGTCCGAGTTTGAAAGATGG

CTTCGGCTATCACTTTTGGATGGTCCCGCGGCGTATTAGCTAGATGGTGAGGTAAC

GGCTCACCATGGCAATGATACGTAGCCGACCTGAGAGGGTAATCGGCCACATTGG

GACTGAGACACGGCCCAAACTCCTACGGGAGGCAGCAGTAGGGAATCTTCCACAA

TGGACGAAAGTCTGATGGAGCAACGCCGCGTGAGTGAAGAAGGGTTTCGGCTCGT

AAAACTCTGTTGTTAAAGAAGAACATATCTGAGAGTAACTGTTCAGGTATTGACGGT

ATTTAACCAGAAAGCCACGGCTAACTACGTGCCAGCAGCCGCGGTAATACGTAGG

TGGCAAGCGTTGTCCGGATTTATTGGGCGTAAAGCGAGCGCAGGCGGTTTTTAA

GTCTGATGTGAAAGCCTTATTCTCAACCGAAGAAGTGCATCGGAAACTGGGAAACT

TGAGTGCAGAAGAGGACAGTGGAACTCCATGTGTAGCGGTGAAATGCGTAGATAT

ATGGAAGAACACCAGTGGCGAAGGGCTGTCTGGTCTGTAACTGACGCTGAGG

CTCGAAAGTATGGGTAGCAAACAGGATTAGATACCCTGGTAGTCCATACCGTAAAC

GATGAATGCTAAGTGTTGGAGGGTTTCCGCCCTTCAGTGCTGCAGCTAACGCATTA

AGCATTCCGCCTGGGGAGTACGGCCGCAAGGCTGAAACTCAAAGGAATTGACGG

GGGCCCGCACAAGCGGTGGAGCATGTGGTTTAATTCGAAGCTACGCGAAGAACCT

TACCAGGTCTTGACATACTATGCAAATCTAAGAGATTAGACGTTCCCTTCGGGGAC

ATGGATACAGGTGGTGCATGGTTGTCGTCAGCTCGTGTCGTGAGATGTTGGGTTA

AGTCCCGCAACGAGCGCAACCCTTATTATCAGTTGCCAGCATTAAGTTGGGCACTC

TGGTGAGACTGCCGGTGACAAACCGGAGGAAGGTGGGGATGACGTCAAATCATCA

TGCCCCTTATGACCTGGGCTACACACGTGCTACAATGGATGGTACAACGAGTTGC

GAACTCGCGAGAGTAAGCTAATCTCTTAAAGCCATTCTCAGTTCGGATTGTAGGCT

GCAACTCGCCTACATGAAGTCGGAATCGCTAGTAATCGCGGATCAGCATGCCGCG

GTGAATACGTTCCCGGGCCTTGTACACACCGCCCGTCACACCATGAGAGTTTGTA

ACACCCAAAGTCGGTGGGGTAACCTTTTAGGAACCATCGACCTAAGGTGGGACAG

ATGATTAGGGTGAAGTCGTAACAAGGTAGCCGTAGGAGAACCTGCGGCTGGATCA

CCTAT

What is claimed is:

1. A method for producing the preparation containing protocatechuic acid (PCA), chlorogenic acid (CGA) and caffeic acid (CA) having a high concentration from coffee cascara comprising steps performed in the following specific order:
  (i) preparing materials including: a coffee cascara ingredient, a composition of complex enzyme-probiotic, a sweetener ingredient, and a water ingredient;
    wherein the sweetener ingredient is a group of soluble sugars, or a group of mixed natural sweeteners;
    the group of soluble sugars including monosaccharides, and disaccharides;
    the group of mixed natural sweeteners including invert sugar, hydrolyzed sugar from starch, honey, and jaggery;
    in which, prepare the coffee cascara ingredient by performing in a specific order from (A) to (C) comprising:
    (A) selecting a coffee fruits with a pH having 4-5, and brix having 9-15° Bx; wherein the coffee fruits is selected from the species group consisting of Arabica coffee (*Coffea arabica* L), Robusta coffee (*Coffea canephora*), Liberia coffee (*Coffea excelsa*), and combinations thereof;
    (B) grinding the coffee fruit, then removing the bean to obtain a coffee cascara; and
    (C) drying the coffee cascara at 40-50° C. until reaching a moisture content of 5%-8% to obtain the coffee cascara ingredient; wherein the coffee cascara ingredient containing chemical components includes PCA having at least 3.5 mg/100 g, CGA having at least 30 mg/100 g, and CA having at least 0.25 mg/100 g;
    in which, prepare the composition of complex enzyme-probiotic by mixing an in-house produced enzyme ingredients with a selected probiotic microorganism ingredients, a mineral ingredients, glycerol, and the water ingredient with at a speed of 200-480 rpm for 10-30 minutes;
    in which, prepare the selected probiotic microorganism ingredients by mixing *Lactobacillus plantarum* LV-1 (SEQ ID No. 1) having at least $1 \times 10^9$ CFU/mL, *Lactobacillus casei* LV-1 (SEQ ID No. 4) having at least $1 \times 10^9$ CFU/mL, *Lactobacillus paracasei* LV-1 (SEQ ID No. 5) having at least $1 \times 10^9$ CFU/mL, and *Saccharomyces cerevisiae* LV-1 (SEQ ID No. 3) having at least $1 \times 10^7$ CFU/mL;
    in which, prepare the mineral ingredients comprising sodium chloride (NaCl) having 2.0-4.5 g/L, magnesium sulfate ($MgSO_4$) having 2.0-4.5 g/L, calcium chloride ($CaCl_2$)) having 1.00-2.25 g/L, manganese sulfate ($MnSO_4$) having 0.01-0.1 g/L, and dipotassium hydrogen phosphate ($K_2HPO_4$) having 0.1-2.0 g/L;
    in which, prepare the in-house produced enzyme ingredients by mixing a first enzyme solution with a second enzyme solution, and a third enzyme solution; wherein a mixing ratio of the first enzyme solution, the second enzyme solution, and third enzyme solution is (3-5):(1-2):(1-3);
    in which, prepare the first enzyme solution by performing in a specific order from (a) to (e) comprising:
    (a) culturing *Lactobacillus plantarum* LV-1 (SEQ ID No. 1) by inoculating a single colony into the nutrient broth, and then incubation at 30° C.-40° C. for 24-48 hours to obtain a first fermentation solution;
    (b) mixing the first fermentation solution with a citrate buffer solution in a ratio of 1:(1-4), stirring at 150-300 rpm for 30-60 minutes at 30° C.-40° C. to obtain a first temporary mixture; wherein the citrate buffer solution has concentration of 20-50 mM, and pH 4.5-6.5;
    (c) centrifuging the first temporary mixture at 10,000×g at 4° C. for 30-60 minutes, collecting the supernatant to obtain a first extracellular solution;
    (d) filtering the first extracellular solution through membrane filter with a pore size of 0.2 μm to obtain a first filtered extracellular solution; and
    (e) filtering the first filtered extracellular solution using a tangential flow filter with a membrane size of 10 kDa to obtain the first enzyme solution;
    in which, prepare the second enzyme solution by performing in a specific order from (a') to (e') comprising:
    (a') culturing *Bacillus subtilis* LV-1 (SEQ ID No. 2) by inoculating a single colony into the nutrient broth, and then incubation at 35° C.-42° C. for 24-48 hours to obtain a second fermentation broth;
    (b') mixing the second fermentation broth with a citrate buffer solution in a ratio of 1:(1-4), stirring at 150-300 rpm for 30-60 minutes at 35° C.-42° C. to obtain a second temporary mixture; wherein the citrate buffer solution has concentration of 20-50 mM and pH 5.0-6.5;

(c') centrifuging the second temporary mixture at 10,000×g at 4° C. for 30-60 minutes, collecting the supernatant to obtain a second extracellular solution;
(d') filtering the second extracellular solution through membrane filter with a pore size of 0.2 μm to obtain a second filtered extracellular solution; and
(e') filtering the second filtered extracellular solution using the tangential flow filter with membrane size of 10 kDa to obtain the second enzyme solution;
in which, prepare the third enzyme solution by performing in a specific order from (a") to (e") comprising:
(a") culturing *Saccharomyces cerevisiae* LV-1 (SEQ ID No. 3) by inoculating a single colony into Yeast Peptone Dextrose (YPD), incubating at 30° C.-40° C. for 24-48 hours to obtain a third fermentation broth;
(b") mixing the third fermentation broth with a citrate buffer solution in a ratio of 1:(1-4), stirring at 150-300 rpm for 30-60 minutes at 30° C.-40° C. to obtain a third temporary mixture; wherein the citrate buffer solution has concentration of 20-50 mM and pH 5.0-6.5:
(c") centrifuging the third temporary mixture at 10,000×g at 4° C. for 30-60 minutes, collecting the supernatant to obtain a third extracellular solution;
(d") filtering the third extracellular solution through membrane filter with a pore size of 0.2 μm to obtain a filtered third extracellular solution; and
(e") filtering the third filtered extracellular solution using the tangential flow filter with membrane size of 10 kDa to obtain the third enzyme solution;
(ii) mixing the coffee cascara ingredient with the sweetener ingredient, and the water ingredient, and then sterilizing at 121° C. for 15 minutes to obtain a foundation mixture;
wherein a mixing ratio of the coffee cascara ingredient, the sweetener ingredient, and the water ingredient is (1-2):(1-2):(7-9);
(iii) admixing the composition of complex enzyme-probiotic with the foundation mixture at step (ii), then hydrolyzing at the temperature of 45° C. to 52° C., combined stirring at an average speed of 100-150 rpm for 12-24 hours to obtain a hydrolyzed mixture;
wherein a mixing ratio of the composition of complex enzyme-probiotic and the base mixture is (1-5): 100;
wherein the hydrolyzed mixture containing chemical components includes:
a PCA having a concentration n times higher than the PCA of the coffee cascara ingredient; wherein n>0;
a CGA having a concentration m times higher than the CGA of the coffee cascara ingredient; wherein m>0; and
a CA having a concentration k times higher than the CA of the coffee cascara ingredient; wherein k>0;
(iv) admixing the composition of complex enzyme-probiotic with the hydrolyzed base mixture at step (iii), then fermenting at 35° C.-40° C., combined stirring at a speed of 100 rpm for 32-38 hours under aeration conditions at an air velocity of 0.5-1.0 vvm to obtain a fermented mixture;
wherein a mixing ratio of the composition of complex enzyme-probiotic and the hydrolyzed base mixture is 1:(15-25);
wherein the fermented mixture containing chemical components includes:
a PCA having a concentration n times higher than the PCA of the coffee cascara ingredient; wherein n'>n;
a CGA having a concentration m times higher than the CGA of the coffee cascara ingredient; wherein m'>m; and
a CA having a concentration k times higher than the CA of the coffee cascara ingredient; wherein k'>k;
(v) filtering the fermented mixture at step (iv) for removing the solid part, and collecting the liquid part is a fermented solution; and
(vi) concentrating the fermented solution at step (v) until the brix having 45° Bx-55° Bx to obtain a preparation containing PCA, CGA and CA having a high concentration from coffee cascara.

2. The method of claim 1, wherein the coffee fruits is Arabica coffee (*Coffea arabica* L).

3. The method of claim 1, wherein at step (ii) the mixing ratio of the coffee cascara ingredient, the sweetener ingredient, and the water ingredient is 1:1:9.

4. The method of claim 1, wherein at step (iii) hydrolyzing at the temperature of 48° C. to 50° C., combined stirring at an average speed of 120-140 rpm for 16-20 hours.

5. The method of claim 1, wherein at step (iv) the mixing ratio of the composition of complex enzyme-probiotic and the hydrolyzed base mixture is 1:20.

6. The method of claim 1, wherein at step (iv) fermenting at 37° C., combined stirring at a speed of 100 rpm for 36 hours under aeration conditions at an air velocity of 0.75 vvm.

7. The method of claim 1, wherein at step (vi) the preparation having 50° Bx.

8. The method of claim 1, wherein at step (iii) the hydrolyzed mixture containing chemical components includes:
the PCA having a concentration (4-11) times higher than the PCA of the coffee cascara ingredient;
the CGA having a concentration (2-7) times higher than the CGA of the coffee cascara ingredient; and
the CA having a concentration (22-28) times higher than the CA of the coffee cascara ingredient.

9. The method of claim 1, wherein at step (iv) the fermented mixture containing chemical components includes:
the PCA having a concentration (12-18) times higher than the PCA of the coffee cascara ingredient;
the CGA having a concentration (8-16) times higher than the CGA of the coffee cascara ingredient; and
the CA having a concentration (75-85) times higher than the CA of the coffee cascara ingredient.

10. The method of claim 1, wherein the sweetener ingredient is sugarcane.

11. The method of claim 1, wherein the composition of complex enzyme-probiotic comprising:
the in-house produced enzyme ingredients having 25%-35% by volume of said composition;
the selected probiotic microorganism ingredients having 45%-55% by volume of said composition;
the mineral ingredients having 3%-7% by volume of said composition;

glycerol having 8%-12% by volume of said composition; and the remainder is the water.

12. The method of claim 11, wherein the composition of complex enzyme-probiotic comprising:

the in-house produced enzyme ingredients having 30% by volume of said composition;

the selected probiotic microorganism ingredients having 50% by volume of said composition;

the mineral ingredients having 5% by volume of said composition;

the glycerol having 10% by volume of said composition; and the remainder is the water.

13. The method of claim 1, wherein the mixing ratio of the first enzyme solution, the second enzyme solution, and third enzyme solution is 5:2:3.

14. The method of claim 1, wherein the in-house produced enzyme ingredients including endoglucanase having 1,500-10,000 U/g protein, polygalacturonase having 1,000-5,500 U/g protein, and amyloglucosidase having 930-5,500 U/g protein.

15. The composition of claim 14, wherein the in-house produced enzyme ingredients including endoglucanase having 5,000-10,000 U/g protein, polygalacturonase having 3,000-5,500 U/g protein, and amyloglucosidase having 3,000-5,500 U/g protein.

* * * * *

```
                               SEQUENCE LISTING

Sequence total quantity: 5
SEQ ID NO: 1           moltype = DNA   length = 1153
FEATURE                Location/Qualifiers
source                 1..1153
                       mol_type = genomic DNA
                       organism = Lactobacillus plantarum
gene                   1153
                       gene = DNA
SEQUENCE: 1
ccctaatcat ctagtcccac cttaagcgag ctgagttcct aaaagagtta ccccaccgac    60
tttgggtgtt acaaactctc atggtgtgac gggcggtgtg tacaaggccc gggaacgtat   120
tcaccgcggc atgctgatcc gcgattacta gcgattccga cttcatgtag gcgagttgca   180
gcctacaatc cgaactgaga atggctttaa gagattagct tactctcgcg agttcgcaac   240
tcgttgtacc atccattgta gcacgtgtgt agcccaggtc ataaggggca tgatgatttg   300
acgtcatccc caccttcctc cggtttgtca ccggcagtct caccagagtg cccaacttaa   360
tgctggcaac tgataataag ggttgcgctc gttgcgggac ttaacccaac atctcacgac   420
acgagctgac gacaaccatg caccacctgt atccatgtcc ccgaagggaa cgtctaatct   480
cttagatttg catagtatgt caagacctgg taaggttctt cgcgtagctt cgaattaaac   540
cacatgctcc accgcttgtg cgggccccg tcaattcctt tgagtttcag ccttgcggcc   600
gtactcccca ggcggaatgc ttaatgcgtt agctgcagca ctgaagggcg aaaccctcc   660
aacacttagc attcatcgtt tacgatatgg actaccaggg tatctaatcc tgtttgctac   720
ccatactttc gagcctcagc gtcagttaca gaccagacag ccgccttcgc cactggtgtt   780
cttccatata tctacgcatt tcaccgctac acatggagtt ccactgtcct cttctgcact   840
caagtttccc agtttccgat gcacttcttc ggttgagccg aaggctttca catcagactt   900
aaaaaaccgc ctgcgctcgc tttacgccca ataaatccgg acaacgcttg ccacctacgt   960
attaccgcgg ctgctggcac gtagttagcc gtggctttct ggttaaaatac cgtcaatacc  1020
tgaacagtta ctctcagata tgttcttctt taacaacaga gttttacgag ccgaaacccct  1080
tcttcactca cgcggcgttg ctccatcaga cttcgtcca ttgtggaaga ttccctactg  1140
ctgcctcccg tag                                                     1153

SEQ ID NO: 2           moltype = DNA   length = 1545
FEATURE                Location/Qualifiers
source                 1..1545
                       mol_type = genomic DNA
                       organism = Bacillus subtilis
gene                   1545
SEQUENCE: 2
agagtttgat cctggctcag gacgaacgct ggcggcgtgc ctaatacatg caagtcgagc    60
ggaccgacgg gagcttgctc ccttaggtca gcggcggacg ggtgagtaac acgtgggtaa   120
cctgcctgta agactgggat aactccggga accggggct aataccggat gcttgattga   180
accgcatggt tcaatcataa aaggtggctt ttagctacca cttgcagatg gaccgcggc   240
gcattagcta gttggtgagg taacggctca ccaaggcgac gatgcgtagc cgacctgaga   300
gggtgatcgg ccacactggg actgagacac ggcccagact cctacgggag gcagcagtag   360
ggaatcttcc gcaatggacg aaagtctgac ggagcaacgc cgcgtgagtg atgaaggttt   420
tcggatcgta aaactctgtt gttagggaag aacaagtacc gttcgaatag gcggtacct    480
tgacgtgtacc taaccagaaa gccacgcta actacgtga agcagccgcg gtaatacgta   540
ggtggcaagc gttgtccgga attattggcg taaagcgcg cgcaggcggt ttcttaagtc   600
tgatgtgaaa gccccggct caaccgggga gggtcattgg aaactgggga acttgagtgc   660
agaagaggag agtggaattc cacgtgtagc ggtgaaatgc gtagagatgt ggaggaacac   720
cagtggcgaa ggcgactctc tggtctgtaa cgactgctgc gtgaaagcg tgggggagcg   780
gaacaggatt agataccctg gtagtccacg ccgtaaacga tgagtgctaa gtgttagagg   840
gtttccgccc ttagtgctg cagcaaacgc attaagcact ccgcctgggg agtacggtcg   900
caagactgaa actcaaagga attgacgggg cccgcacaa gcggtggagc atgtggttta   960
attcgaagca acgcgaagaa ccttaccagg tcttgacatc ctctgcaac cctagagata  1020
```

```
gggcttcccc ttcggggca gagtgacagg tggtgcatgg ttgtcgtcag ctcgtgtcgt   1080
gagatgttgg gttaagtccc gcaacgagcg caacccttga tcttagttgc cagcattcag   1140
ttgggcactc taaggtgact gccggtgaca aaccggagga aggtggggat gacgtcaaat   1200
catcatgccc cttatgacct gggctacaca cgtgctacaa tgggcagaac aaagggcagc   1260
gaagccgcga ggctaagcca atcccacaaa tctgttctca gttcggatcg cagtctgcaa   1320
ctcgactgcg tgaagctgga atcgctagta atcgcggatc agcatgccgc ggtgaatacg   1380
ttcccgggcc ttgtacacac cgcccgtcac accacgagag tttgtaacac ccgaagtcgg   1440
tgaggtaacc ttttggagcc agccgccgaa ggtgggacag atgattgggg tgaagtcgta   1500
acaaggtagc cgtatcggaa ggtgcggctg gatcacctcc tttct                  1545

SEQ ID NO: 3           moltype = DNA   length = 748
FEATURE                Location/Qualifiers
source                 1..748
                       mol_type = genomic DNA
                       organism = Saccharomyces cerevisiae
gene                   748
SEQUENCE: 3
aagaaattta ataattttga aaatggattt ttttgttttg gcaagagcat gagagcttt    60
actgggcaag aagacaagag atggagagtc cagccgggcc tgcgcttaag tgcgcggtct   120
tgctaggctt gtaagtttct ttcttgctat tccaaacggt gagagatttc tgtgcttttg   180
ttataggaca attaaaaccg tttcaataca acacactgtg gagttttcat atctttgcaa   240
cttttcttt gggcattcga gcaatcgggg cccagagtga acaaacacaa acaattttat    300
ctattcatta aatttttgtc aaaaacaaga attttcgtaa ctggaaattt taaaaatatt   360
aaaaactttc aacaacggat ctcttggttc tcgcatcgat gaagaacgca gcgaaatgcg   420
atacgtaatg tgaattgcag aattccgtga atcatcgaat ctttgaacgc acattgcccc   480
cttggtattc caggggggta gcctgtttga gcgtcatttc cttctcaaac attctgtttg   540
gtagtgagtg atactctttg gagttaactt gaaattgctg gccttttcat tggatgtttt   600
ttttccaaag agaggtttct ctgcgtgctt gaggtatttt gcaagtacgg tcgttttagg   660
ttttaccaac tgcggctaat cttttttata ctgagcgtat ggaacgttta tcgataagaa   720
gagagcgtgt aggcaacaat gttcttaa                                      748

SEQ ID NO: 4           moltype = DNA   length = 1559
FEATURE                Location/Qualifiers
source                 1..1559
                       mol_type = genomic DNA
                       organism = Lactobacillus casei
SEQUENCE: 4
gagagtttga tcctggctca ggacgaacgc tggcggcgtg cctaatacat gcaagtcgaa   60
cgaactctgg tattgattgg tgcttgcatc atgatttaca tttgagtgag tggcgaactg   120
gtgagtaaca cgtgggaaac ctgcccagaa gcggggggata acacctggaa acagatgcta   180
ataccgcata caacttggac cgcatggtcc gagtttgaaa gatggcttc ggctatcact    240
tttggatggt cccgcggcgt attagctaga tggtgaggta acggctcacc atggcaatga   300
tacgtagccg acctgagagg gtaatcggcc acattggact gagacacggc ccaaactcc    360
tacgggaggc agcagtaggg aatcttccac aatggacgaa agtctgatgg agcaacgccg   420
cgtgagtgaa gaagggtttc ggctcgtaaa actctgttgt taagaagaa catatctgag    480
agtaactgtt caggtattga cggtatttaa ccagaaagcc acggctaact acgtgccagc   540
agccgcggta atacgtaggt ggcaagcgtt gtccggattt atggggcgta aagcgagcgc   600
aggcggtttt ttaagtctga tgtgaaagcc ttattctcaa ccgaagaagt gcatcggaaa   660
ctgggaaact tgagtgcaga agaggacagt ggaactccat gtgtagcggt gaaatgcgta   720
gatatatgga agaacaccag tggcgaaggc ggctgtctgg tctgtaactg acgctgaggc   780
tcgaaagtat gggtagcaaa caggattaga taccctgtag tccataccg taaacgatgc    840
atgctaagtg ttggagggtt tccgcccttc agtgctgcag ctaacgcatt aagcattccg   900
cctggggagt acgaccgcaa ggctgaaact caaaggaatt gacggggcc cgcacaagcg    960
gtggagcatg tggtttaatt cgaagctacg cgaagaacct taccaggtct tgacatacta   1020
tgcaaatcta agagattaga cgttcccttc ggggacattg gatacaggtgg tgcatggttg   1080
tcgtcagctc gtgtcgtgag atgttgggtt aagtcccgca acgagcgcaa cccttattat   1140
cagttgccag cattaagttg gcactctggg tgagactgcc ggtgacaaac cggaggaagt   1200
tggggatgac gtcaaatcat catgccctt atgacctggg ctacacacgt gctacaatgg    1260
atggtacaac gagttgcgaa ctcgcgagag taagctaatc tcttaaagcc attctcagtt   1320
cggattgtag gctgcaactc gcctacatga agtcggaatc gctagtaatc gcggatcagc   1380
atgccgcggt gaatacgttc ccgggccttg tacacaccgc ccgtcacacc atgagagttt   1440
gtaacaccca aagtcggtgg ggtaaccttt taggaaccat cggcctaagg tgggacagat   1500
gattagggtg aagtcgtaac aaggtagccg taggagaacc tgcggctgga tcacctcct   1559

SEQ ID NO: 5           moltype = DNA   length = 1554
FEATURE                Location/Qualifiers
source                 1..1554
                       mol_type = genomic DNA
                       organism = Lactobacillus paracasei
SEQUENCE: 5
gtttgatcct ggctcaggac gaacgctggc ggcgtgccta atacatgcaa gtcgaacgaa   60
ctctggtatt gattggtgct tgcatcatga tttacatttg agtgagtggc gaactggtga   120
gtaacacgtg ggaaacctgc ccagaagcgg ggataacac ctggaaacag atgctaatac    180
cgcataacaa cttggaccgc atggtccgag tttgaaagat ggcttcggct atcacttttg   240
gatggtcccg cggcgtatta gctagatggt gaggtaacgg ctcaccatgg caatgatacg   300
tagccgacct gagagggtaa tcggccacat tgggactgag acacgcccca aactcctacg   360
ggaggcagca gtagggaatc ttccacaatg gacgaaagtc tgatggagca acgccgcgtg   420
agtgaagaag ggtttcggct cgtaaaactc tgttgttaaa gaagaacata tctgagagta   480
actgttcagg tattgacggt atttaaccag aaagccacgg ctaactacgt gccagcagcc   540
```

-continued

```
gcggtaatac gtaggtggca agcgttgtcc ggatttattg ggcgtaaagc gagcgcaggc    600
ggttttttaa gtctgatgtg aaagccttat tctcaaccga agaagtgcat cggaaactgg    660
gaaacttgag tgcagaagag gacagtggaa ctccatgtgt agcggtgaaa tgcgtagata    720
tatggaagaa caccagtggc gaaggcggct gtctggtctg taactgacgc tgaggctcga    780
aagtatgggt agcaaacagg attagatacc ctggtagtcc ataccgtaaa cgatgaatgc    840
taagtgttgg agggtttccg cccttcagtg ctgcagctaa cgcattaagc attccgcctg    900
gggagtacgg ccgcaaggct gaaactcaaa ggaattgacg ggggcccgca caagcggtgg    960
agcatgtggt ttaattcgaa gctacgcgaa gaaccttacc aggtcttgac atactatgca   1020
aatctaagag attagacgtt cccttcgggg acatggatac aggtggtgca tggttgtcgt   1080
cagctcgtgt cgtgagatgt tgggttaagt cccgcaacga gcgcaaccct tattatcagt   1140
tgccagcatt aagttgggca ctctggtgag actgccggtg acaaaccgga ggaaggtggg   1200
gatgacgtca aatcatcatg ccccttatga cctgggctac acacgtgcta caatggatgg   1260
tacaacgagt tgcgaactcg cgagagtaag ctaatctctt aaagccattc tcagttcgga   1320
ttgtaggctg caactcgcct acatgaagtc ggaatcgcta gtaatcgcgg atcagcatgc   1380
cgcggtgaat acgttcccgg gccttgtaca caccgcccgt cacaccatga gagtttgtaa   1440
cacccaaagt cggtggggta accttttagg aaccatcgac ctaaggtggg acagatgatt   1500
agggtgaagt cgtaacaagg tagccgtagg agaacctgcg gctggatcac ctat         1554
```